(12) United States Patent
Shackleford et al.

(10) Patent No.: US 6,968,275 B1
(45) Date of Patent: Nov. 22, 2005

(54) PIPELINED DIGITAL CIRCUIT FOR DETERMINING THE CONFORMATIONAL ENERGY OF A FOLDED PROTEIN

(75) Inventors: J Barry Shackleford, Sunnyvale, CA (US); Gregory S. Snider, Mountain View, CA (US); Richard J Carter, Menlo Park, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 274 days.

(21) Appl. No.: 10/080,018

(22) Filed: Feb. 22, 2002

(51) Int. Cl.[7] .................. G01N 33/48; G05B 15/00
(52) U.S. Cl. ............................ 702/27; 700/1
(58) Field of Search .............. 702/27; 700/1

(56) References Cited

U.S. PATENT DOCUMENTS

| | | | | |
|---|---|---|---|---|
| 5,572,212 A | * | 11/1996 | Levinson et al. | 341/162 |
| 5,579,250 A | | 11/1996 | Balaji et al. | 364/496 |
| 5,842,151 A | | 11/1998 | Noguchi | 702/27 |
| 5,878,373 A | | 3/1999 | Cohen et al. | 702/22 |
| 5,884,230 A | | 3/1999 | Srinivasan et al. | 702/22 |
| 6,080,204 A | * | 6/2000 | Mendel | 716/7 |
| 6,125,331 A | | 9/2000 | Toh | 702/19 |
| 6,282,635 B1 | * | 8/2001 | Sachs | 712/215 |

OTHER PUBLICATIONS

Sali et al., Kinetics of Protein Folding J.Mol. Biol. vol. 235 pp. 1614-1636 (1994).*
Unger et al. Genetic Algorithms for Protein Folding Simulations J. Mol. Biol. vol. 231 pp. 75-81 (1993).*
"Computer Organization and Design: The Hardware/Software Interface", 2nd Edition, David A. Patterson and John L. Hennessy, 1998, p. 436.

* cited by examiner

Primary Examiner—John S. Brusca

(57) ABSTRACT

The present invention provides a method and apparatus to significantly accelerate the searching process based on the Monte Carlo principle and the lattice model. Specifically, the energy status of a lattice-based protein conformation is evaluated by modeling the folding process through a pipelined digital circuit using a number of state machines. The pipelined digital circuit reduces the time required for the determination of the energy status of a particular conformation and, therefore, significantly accelerates the searching speed for the lowest energy status. The present invention also permits real-time tuning of problem parameters by the experimenter.

20 Claims, 12 Drawing Sheets

PIPELINED DIGITAL CIRCUIT FOR DETERMINING THE CONFORMATIONAL ENERGY OF A FOLDED PROTEIN

TECHNICAL FIELD

The technical field generally relates to a method and apparatus for the simulation and prediction of protein folding.

BACKGROUND

Proteins are the building blocks of all living organisms. A single cell may contain many hundreds of proteins to perform various functions such as digesting food, producing energy, regulating chemical reactions, and building other proteins.

Structurally, proteins are linear polymers of amino acids also referred to as "polypeptides." There are 20 different naturally occurring amino acids involved in the biological production of proteins. All amino acids contain carbon, hydrogen, oxygen, and nitrogen. Some also contain sulfur. The amino acids are assembled into a polypeptide chain on the ribosome using the codon sequence on mRNA as a template. As shown in FIG. 1, the resulting linear chain 101 forms secondary structures 103 through the formation of hydrogen bonds between amino acids in the chain. Through further interactions among amino acid side groups, these secondary structures 103 then fold into a three-dimensional structure 105. Therefore, protein structure is largely specified by amino acid sequence, but how one set of interactions of the many possible occurs is not yet fully understood.

FIG. 2 shows a conventional chemical representation of a part of a polypeptide, consisting of three amino acids. Each amino acid (or residue) consists of a common main chain part, containing the atoms N, C, O, $C_\alpha$, and two hydrogen atoms, and a specific side chain R, which is also called a "pendant group." The pendant groups (R1, R2 and R3 in FIG. 2) are always attached to the alpha carbon ($C_\alpha$) atom. Amino acids can be divided into several classes based on size and other physical and chemical properties of their pendant groups. The main classification concerns the hydropathy of the residues, i.e., into hydrophobic residues which do not like to interact with the solvating water molecules, and into hydrophilic residues which have the ability to form hydrogen bonds with water. The hydrophilic residues can be further divided into charged residues which have a net electric charge (either positive or negative) and polar residues who don't have a net charge but have non-uniform charge distribution.

The amino acids are joined through the peptide bond, i.e., the planer CO-NH group. The planar peptide bond may be represented as depicted in FIG. 3. Because the O=C and the C—N atoms lie in a relatively rigid plane, free rotation does not occur about these axes. Hence, a plane 107 or 107', schematically depicted in FIG. 3 by the dotted lines, and sometimes referred to as an "amide plane" or "peptide plane" is formed, wherein lie the oxygen (O), carbon (C), nitrogen (N), and hydrogen (H) atoms of a given amino acid or residue. At opposite corners of this amide plane 107 are located the alpha-carbon ($C_\alpha$) atoms, which serve as swivel points or centers for a polypeptide chain. The two dihedral angles, $\phi$ and $\psi$ on each side of the $C_\alpha$ atom, are the main degrees of freedom in forming the three-dimensional trace of the polypeptide chain. Due to steric restrictions, these angles can have values only in specific domains in the $\phi$-$\psi$ space. The pendant groups R branch out of the main chain from the $C_\alpha$ atom. These pendant groups, ranging in size from one to 18 atoms, have additional degrees of freedom, called $\chi_i$ angles, which enable them to adjust their local conformation to their environment.

Thus, a polypeptide structure bends, folds or flexes at each $C_\alpha$ atom swivel point. In a particular environment, and depending upon the particular side chains that may be attached to the polypeptide, some of these bends or folds may be stable, i.e. the $\phi$ and $\psi$ angles will not change. In many environments, however, the $\phi$ and $\psi$ angles will not be stable, and the polypeptide chain will dynamically fold and bend, as they are subjected to external or internal forces. Such forces may originate from numerous sources, such as ions, or molecules in the medium within which the polypeptide is located (external forces) that either attract or repel a given atom or group of atoms within the polypeptide. Often, however, these forces originate from within the polypeptide itself, or within one of its pendant groups, as the chain folds back on itself and one residue or pendant group of the polypeptide comes in close proximity to another residue or pendant group chain of the polypeptide.

In general, just as a flexible rope can assume an infinite number of shapes, a polypeptide chain can conceptually also assume an infinite number of shapes. Many of the possible shapes, however, are unstable, because the internal and external molecular attraction and/or repulsion forces will not permit such shapes to persist. These forces act to move or change the polypeptide conformation away from unstable conformations toward a stable conformation. A stable conformation is one where the internal and external molecular attraction and/or repulsion forces fail to destabilize or push the existing conformation toward another conformation.

Most polypeptide structures exhibit several conformations that are stable, some more so than others. The most stable conformations are the most probable. A conformation may change from one stable conformation to another through the application of sufficient energy to cause the change. Given the opportunity to freely move, fold and/or bend, a given polypeptide chain will eventually assume a stable conformation. The most probable conformation that is assumed is the one that would take the most energy to undo or, in other words, the conformation that has the lowest free energy.

Currently, there are two experimental methods to determine the three-dimensional structure of a protein. The first method is X-ray crystallography. The protein has to be first isolated, highly purified, and incubated under certain conditions to form a crystal. The protein is then exposed to X-ray radiation and the pattern of reflections is recorded. From these reflections, it is possible to deduce the actual three-dimensional electron density of the protein and thus to solve its structure. The second method is nuclear magnetic resonance (NMR), which is currently applicable only to small-size proteins. The underlying principle is that, by exciting one nucleus and measuring the coupling effect on a neighboring nucleus, one can estimate the distance between these nuclei. A series of such measured, pairwise distances is used to reconstruct the protein structure. Both methods are inherently time and labor consuming.

With the rapid progress in obtaining genetic information from human and other organisms, the primary sequences of a large number of proteins have been determined. However, to effectively utilize the ever-expanding database of primary sequence information, it is necessary to predict the three-dimensional structure of a protein based on its primary sequences. For example, in order to design a drug to block an active site in a receptor protein, one has to simulate the interaction of the drug with the amino acid residues in the active site. The drug design is possible only when the three-dimensional structure of the protein is determined.

A number of computational approaches have been developed to calculate the three-dimensional structure based on the assumption that the native structure of a protein has the lowest free energy among all the possible conformations of the chain. Two principal methods are currently in use, the molecular dynamics method and the Monte Carlo method.

In the molecular dynamics method, an all-atom description is usually used. Forces acting on each atom at a particular state of the system are calculated using an empirical force field. Atoms are then allowed to move with the accelerations resulting from forces according to Newton's second law. Once the atoms have moved far enough for the forces to have changed significantly, the forces are recalculated and new accelerations applied. In practice, forces have to be recalculated approximately every $10^{-15}$ second. Even with powerful supercomputers only very short time periods can be simulated, much shorter than the actual folding process. Hence, this method can currently be used only to describe some sub-folding events (e.g., the initiation of the process, or re-folding after a slight perturbation) rather than the whole process.

The Monte Carlo method is usually used with simplified models. The procedure starts with an initial conformation and makes a random "move" to another conformation. The energy of the new conformation is compared with the energy of the old one. If the new conformation is better, meaning it has a lower free energy, the new conformation replaces the old one. If the new conformation has a higher energy, it is subject to a non-deterministic decision based on the amount of the energy gained, such that a larger energy gain makes the acceptance more unlikely. If the new conformation is not accepted, the old conformation is retained. The current conformation is then subject to another random change and the procedure iterates. The Monte Carlo methods have been applied in many protein studies for different tasks with different levels of success. Yet, as a search method, even on simple models, the method is not powerful enough in most cases to find the lowest free energy conformation starting from a random conformation.

Based on the Monte Carlo principle, Lau and Dill developed a simplified two-dimensional square lattice model for protein folding (Lau. K. F. and Dill K. A. Proc. Natl. Acad. Sci. USA 87:638–642, 1990). Unger and Moult have described the application of a genetic algorithm to discover the minimum-energy conformation for such a lattice-constrained protein (Unger R. and Moult J. Proceedings of the Fifth International conference on Genetic algorithms, Forrest S. ed., pp. 581–588, 1993). However, the problem has a nondeterministic polynomial solution, which means that when a solution is given it can not be verified in polynomial time, which is computationally unfeasible for even the fastest computers. Additionally, the prior solutions are software-based emulations, and thus have been very time consuming when implemented on conventional computers.

SUMMARY

The present invention provides a method and apparatus to significantly accelerate the process of searching for the minimum-energy conformation of a protein using the Monte Carlo principle and the lattice model of Lau and Dill. Specifically, the energy status (defined as the "folding cost") of a lattice-based protein conformation is evaluated by modeling the folding process through a pipelined digital circuit. The pipelined digital circuit uses a plurality of state machines to record energy expenses of each amino acid residue during the formation of a particular conformation. The folding cost of a "default" conformation is then compared to that of a new conformation. If the folding cost of the new conformation is lower than the folding cost of the default conformation, the new conformation becomes the default conformation. If the folding cost of the new conformation is higher than the folding cost of the default conformation, the default conformation is retained. This process is repeated until the genetic algorithm search process fails to produce new, lower-cost conformations within a time frame determined by the experimenter. Compared to a purely software-based program, the utilization of the pipelined digital circuit significantly reduces the time required for the determination of the energy status of a particular conformation, and, therefore, significantly accelerates the searching speed for the minimal-energy status and permits real-time tuning of problem parameters by the experimenter.

BRIEF DESCRIPTION OF THE DRAWINGS

The specification refers to the following drawings, in which like numerals refer to like elements, and in which.

DETAILED DESCRIPTION

Figure 1:
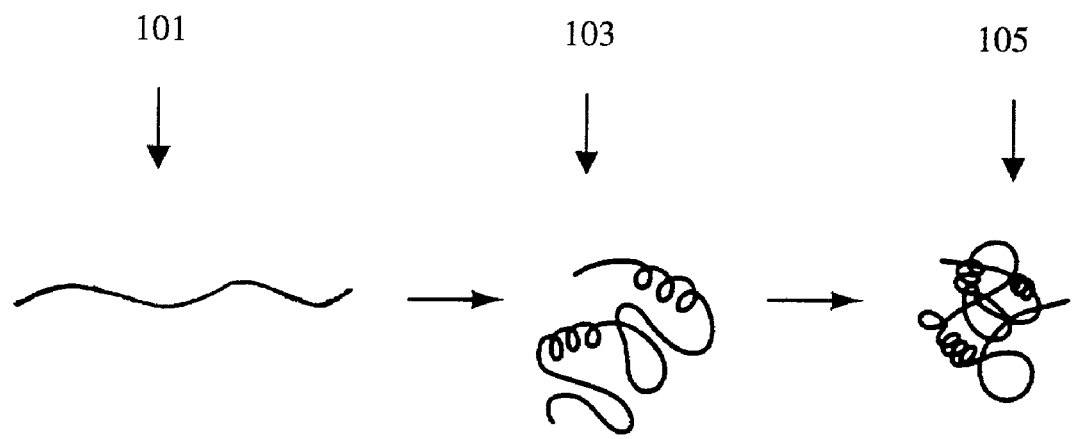
FIG. 1 generally illustrates a protein folding process from a linear conformation to a complex three-dimensional conformation.
Figure 2:
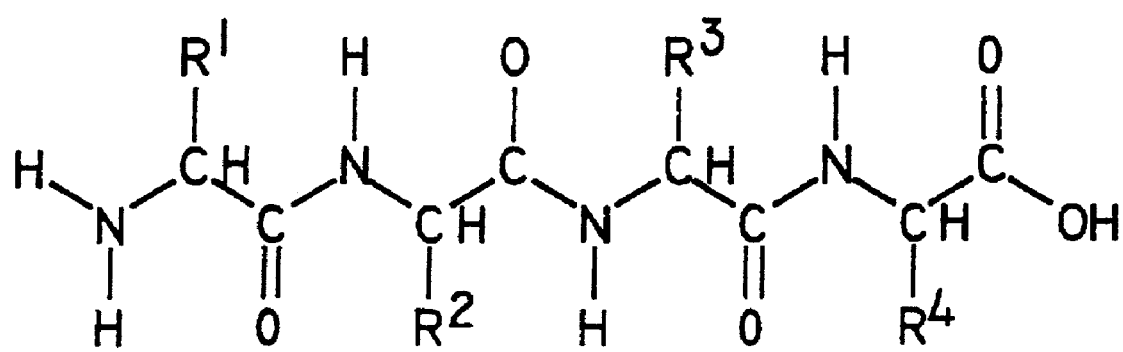
FIG. 2 illustrates a representative polypeptide chain.
Figure 3:
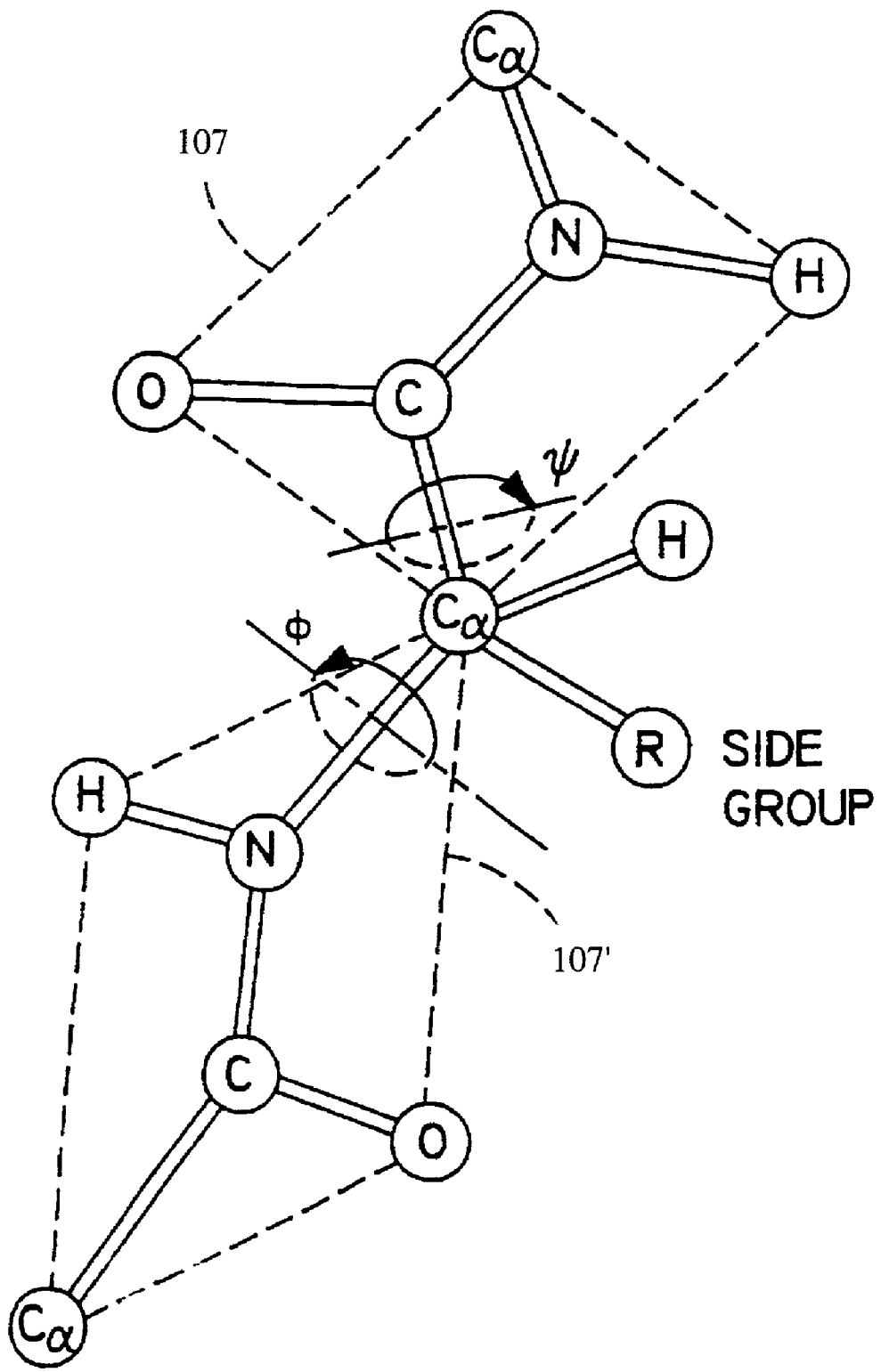
FIG. 3 generally illustrates the φ and ψ angles on either side of the alpha carbon ($C_\alpha$) atom.
Figure 4:
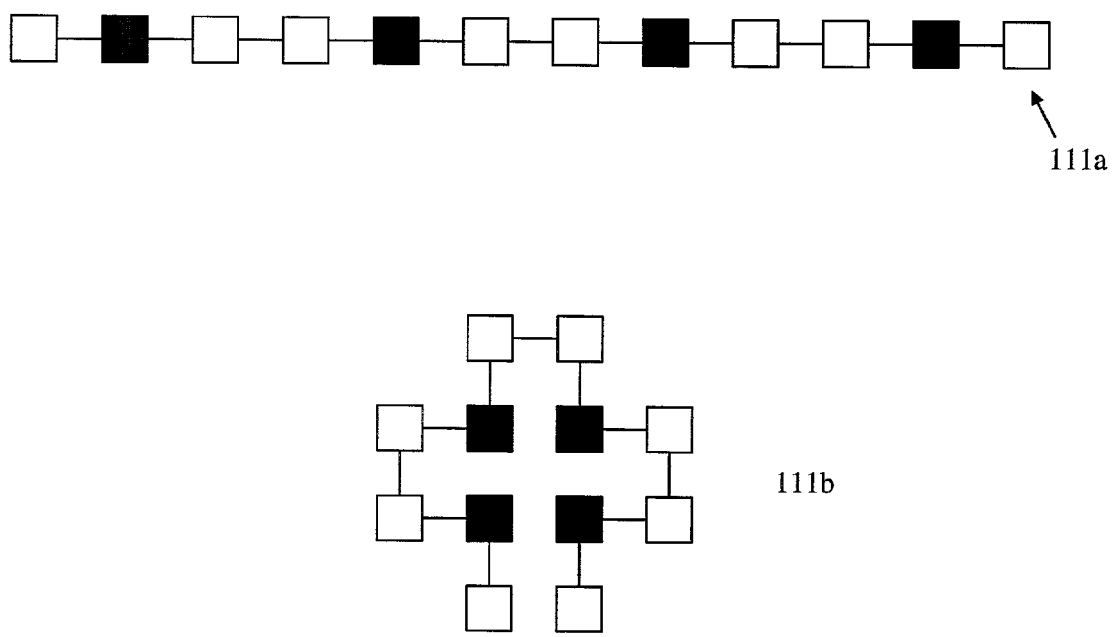
FIG. 4 generally illustrates folding a simple, linear protein in a 2-dimensional lattice.

The present invention provides a method and apparatus to significantly accelerate the searching process based on the Monte Carlo principle and the lattice model. In this model, each protein 111 is a linear chain of a specific sequence of n discrete amino acids. As discussed, each amino acid can be either of two types: hydrophobic residues (filled squares) which are repelled by the solvating water molecules, or hydrophilic residues (open squares) which can form hydrogen bonds with surrounding water molecules, as illustrated in FIG. 4. With reference now to FIG. 4, when a protein chain 111a is allowed to fold and seek its lowest energy conformation, e.g., conformation 111b, the hydrophobic residues will tend to be clustered together in the center and the hydrophilic residues will tend to be on the outside. A chain conformation is represented as a self-avoiding walk on a two-dimensional (2-d) square lattice. Thus, each amino acid is represented as simply occupying one lattice site, connected to its chain neighbor(s), and unable to occupy a site filled by any other residue.

The randomization of the Monte Carlo method is implemented in a genetic algorithm. A simple child-evaluation function that will drive the genetic algorithm towards solutions of this kind can be constructed by modeling the conformational energy of the protein. Since smaller values of the function will represent more-fit offspring, the term "cost function" is used to refer to this type of inverted fitness function. The adaptation of the genetic algorithm pipeline to handle a cost function is simple: the worst parent becomes that parent with the largest (rather than smallest) cost evaluation and the child survives if its cost is less than that of the worst parent. The survival of the child chromosome implies the demise of the parent with the replacement of its pattern, e.g., in the form of bits, in population memory by that of the surviving child's bit pattern.

The protein energy cost function is calculated as follows: if no hydrophobic residues are adjacent in the lattice and there is no multiple occupancy of any lattice position, then the energy is defined to be zero. For every pair of adjacent hydrophobic residues in the lattice, the energy is reduced by one. Adjacent hydrophobic residues on the chain are not counted because it simplifies a hardware implementation and has no effect on the functional performance due to being a constant for any given chain that is being folded. Any given chain has a relative minimum that is dependant upon its particular arrangement of hydrophilic and hydrophobic residues, and the adjacencies of these residues is determined by the particular minimum of the particular protein chain. In the event of folding "collisions" where two or more residues try to occupy the same lattice position, the number of collisions is multiplied by a constant (larger than the greatest possible number of adjacent hydrophobic pairs) and added to the energy.

As shown in FIG. 4, the linear conformation of the simple, linear protein 111a is defined to have a free energy of zero. When folded, as shown by the protein 111b, there are four adjacent hydrophobic residue pairs, each pair reducing the energy by 1, for a total energy of −4. (Note that "adjacency" is defined here to mean "next to", either horizontally or vertically on the page, but not diagonally.)

Figure 5:
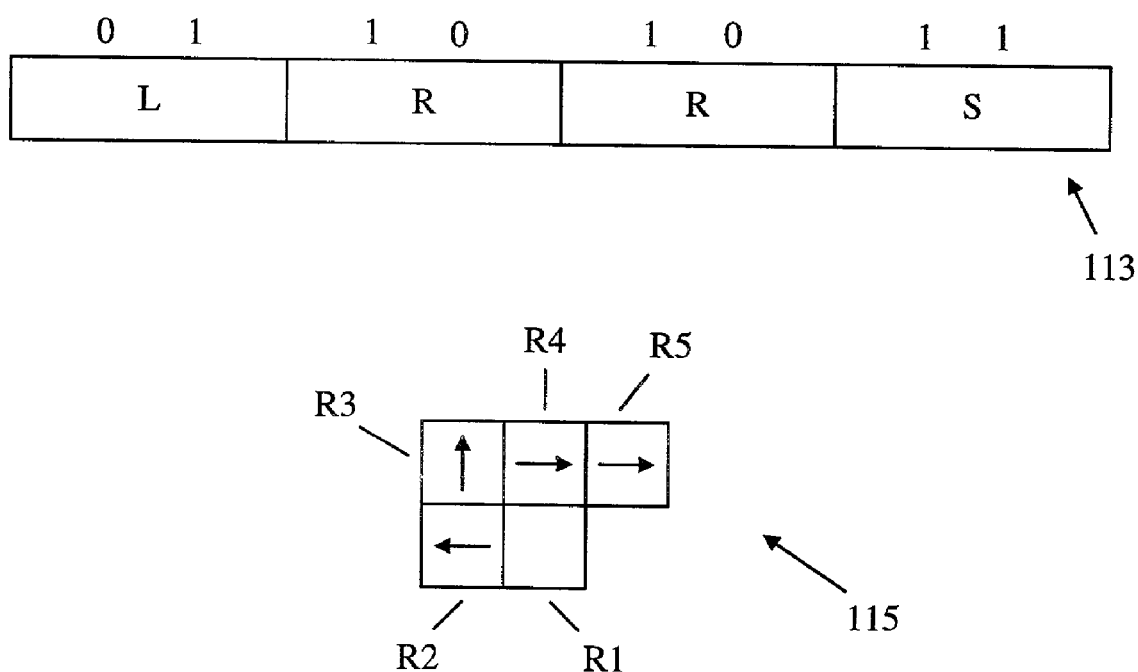
FIG. 5 generally illustrates the chromosome data format for a 2-d lattice protein folding problem, such as illustrated in FIG. 4.

To facilitate the computation of the folding process via genetic algorithm, each protein conformation is digitalized as a "chromosome", designated in FIG. 5 by the reference numeral 113. The chromosome data format for the 2-d lattice protein folding problem is also shown in FIG. 5 and designated therein by the reference numeral 115. For the 2-d problem there are three folding choices at each peptide bond between the residues: straight, left, and right, each represented by respective arrows. It should be understood to those skilled in the art that in the 3-d version of the problem, up and down arrows would be added. Each folding choice is assigned a code as shown in Table I.

TABLE I

Protein folding code in a 2-d lattice model

| Folding direction | Code |
| --- | --- |
| Straight | 00 |
| Left | 01 |
| Right | 10 |
| Straight | 11 |

For a protein with n residues there are $3^{(n-1)}$ possible conformations, meaning $3^{(n-1)}$ possible chromosomes 113. For example, in the 5-residue protein 115 illustrated in FIG. 5, the solution space is $3^{(5-1)}=81$ different chromosomes 113. Encoding each fold as a pair of bits, as shown in FIG. 5, means that the chromosome length will be 2(n-1) bits. It should be noted that there are no coding bits for the first residue of a protein, and that, therefore, the 5-residue protein 115 has a chromosome length of 8 bits. For a 36-residue problem, the chromosome has a length of 70 bits and a solution space of $5 \times 10^{16}$.

For the 3-d problem there are five folding choices at each peptide bond between the residues: straight, left, right, up, and down. Each folding choice is assigned a code as shown in Table II.

TABLE II

Protein folding code in a 3-d lattice model

| Folding direction | Code |
| --- | --- |
| Straight | 000 |
| Left | 001 |
| Right | 010 |
| Straight | 011 |
| Straight | 100 |
| Up | 101 |
| Down | 110 |
| Straight | 111 |

In the 3-d version of the problem, a 5-residue protein has $5^{(n-1)}$ possible conformations, and $5^{(n-1)}$ possible chromosomes 113. With each chromosome having a bit-length of 3(n-1), a 3-d 5-residue protein has a chromosome length of 12 bits and 625 possible conformations or chromosomes 113. A 36-residue protein, therefore, has a chromosome length of 105 bits and a solution space of $2.9 \times 10^{24}$.

Figure 6:
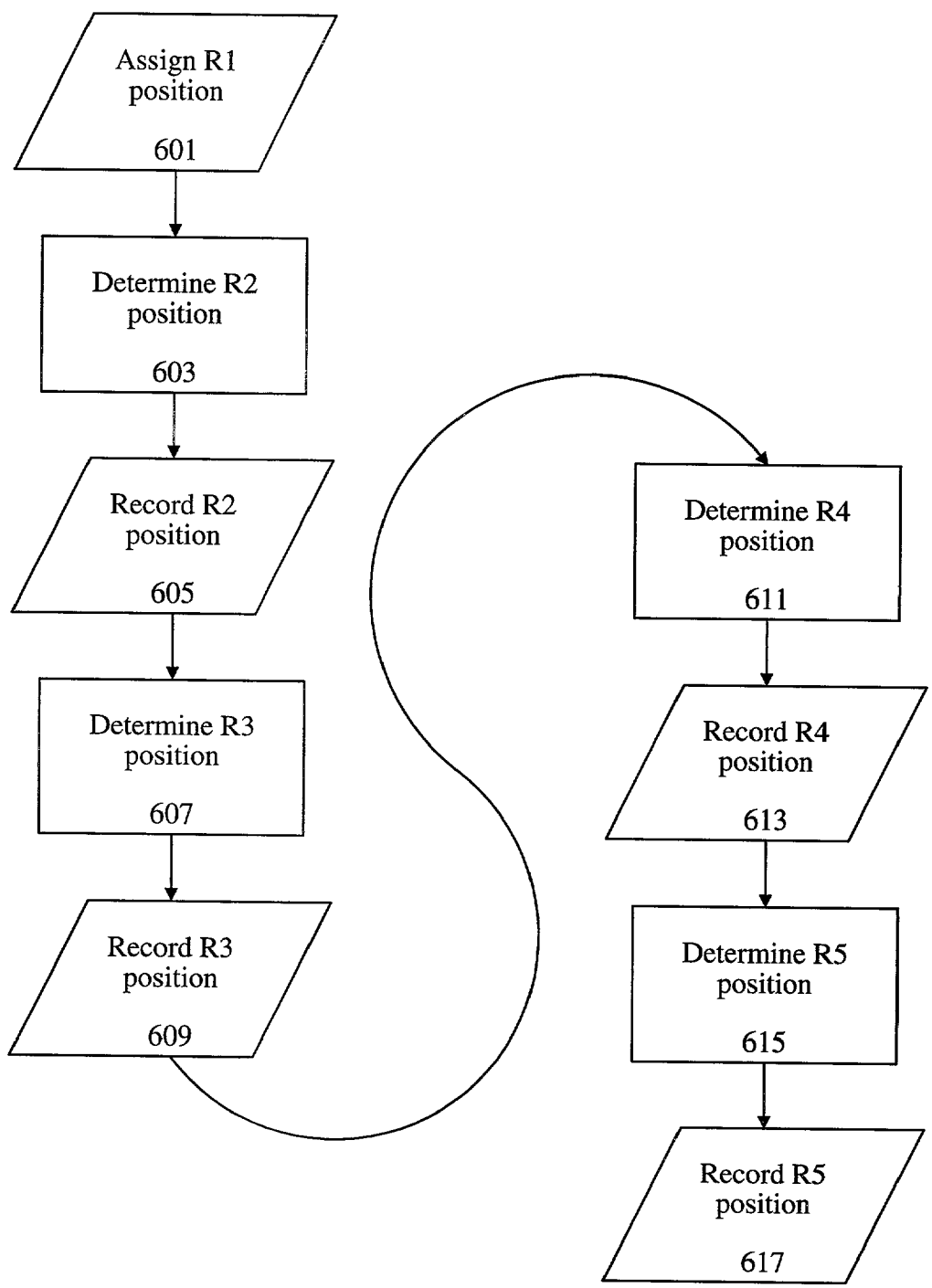
FIG. 6 illustrates a flowchart showing the generation of a chromosome from a folding conformation, such as the 2-d lattice protein folding problem illustrated in FIG. 5.

A further illustration of the encoding process of the 2-d 5-residue protein 115 is shown in FIG. 6. In the methodology set forth in FIG. 6, the first residue R1 is arbitrarily assigned a starting position which is not coded (step 601). The position of the second residue R2 is then determined relative to the position of R1 (step 603) and is recorded by the first two bits in chromosome 113 (step 605). Since R2 folds to the left of R1, as set forth in FIG. 5, its position is coded as 01 according to Table I. The position of the third residue R3 is then determined relative to the position of R2 (step 607), and is recorded by the next two bits in the chromosome 113 (step 609). In the example of FIG. 5, R3 folds to the right of R2 and is, therefore, coded as 10 in the chromosome. The process is repeated, i.e., the position of the fourth residue R4 is determined (step 611), recorded (step 613), the position of the fifth residue R5 determined (step 615) and the last residue recorded in the chromosome (617).

Figure 7:
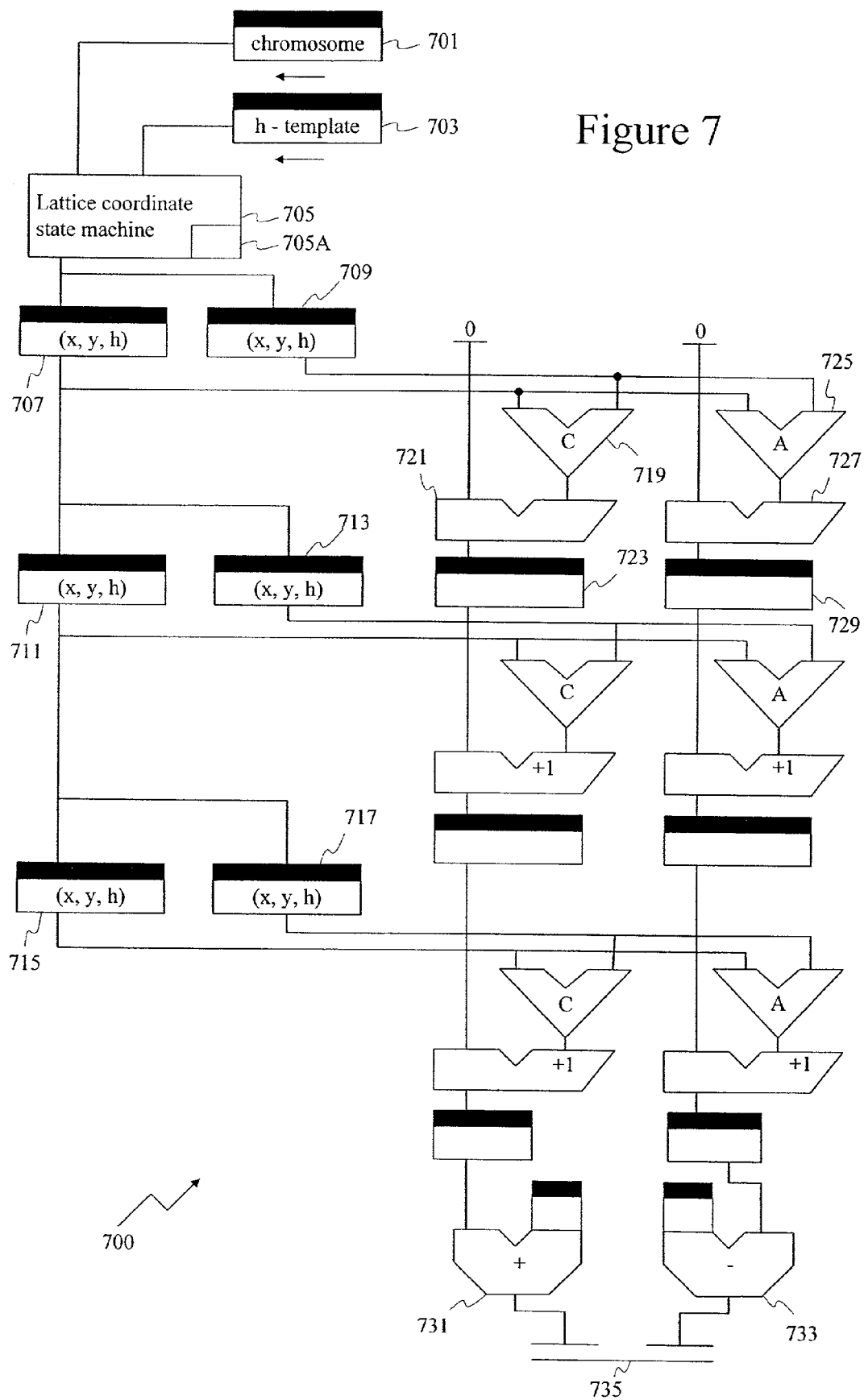
FIG. 7 illustrates a pipelined digital circuit design for solving 2-d lattice protein folding problems, pursuant to the teachings of the present invention.

Pipelined digital circuitry pursuant to the present invention is shown in FIG. 7 and generally designated by the reference numeral 700. As is understood in the art, the pipeline 700 has a latency of 2 n, and an initiation interval of n for a protein with n residues. The folding cost algorithm is built around the lattice coordinates of the folded protein. To obtain these coordinates, a chromosome 701 is shifted two bits per clock cycle into a lattice coordinate state machine 705, together with a template of hydropathy information for each residue (an h-template 703). As a function of the chromosome's folding directions, residue coordinates along with a hydrophobic or hydrophilic marking bit will emerge from the state machine as a combined coordinate with a format of (x, y, h). In this format, x and y correspond to the x-axis and y-axis coordinates of the residue in the 2-d lattice, while h corresponds to the hydrophobic or hydrophilic marking bit which is either a "p" for a hydrophobic residue or an "b" for hydrophilic residues. It should be noted that since the first residue in the protein is not coded by the chromosome, the first residue is always assigned a lattice coordinate of x=0, y=0 as a starting residue in the folding process.

For the 3-d problem, the state machine produces a combined coordinate with a format (x, y, z, h). As with the 2-d format, x and y correspond to the x-axis and y-axis of the residue, while h corresponds to the hydrophobic or hydrophilic marking bit. The z bit corresponds to the z-axis of the residue and is determined by directions up and down, as is understood in the art.

Figure 8:
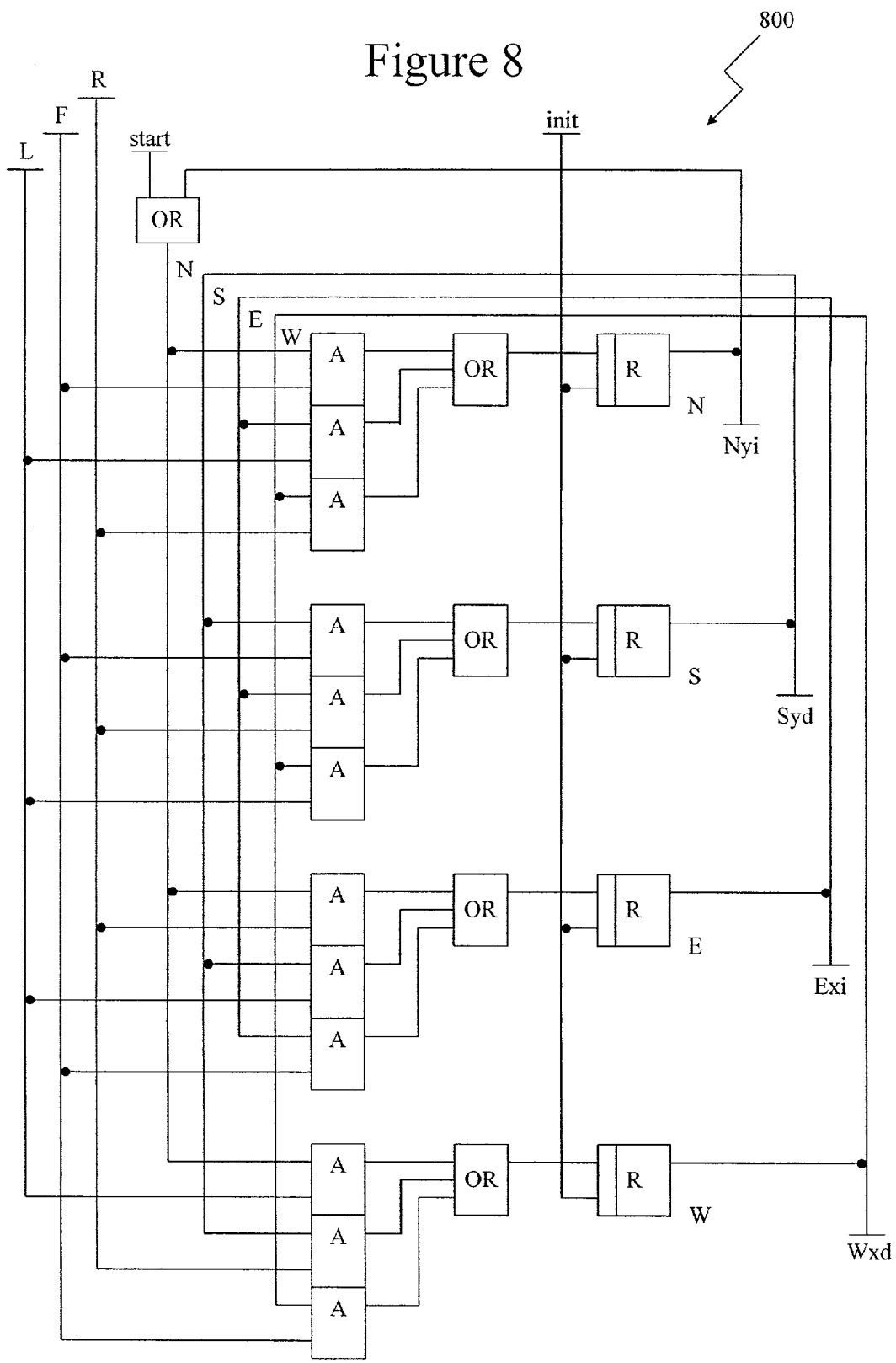
FIG. 8 illustrates a representative state machine used in connection with the pipeline digital circuit of the present invention.

The 2-d state machine 705 of FIG. 7 is illustrated in more detail in FIG. 8. A decoder 705a within the state machine 705 translates the pair of bits that is the directional code, according to Table I, into one of three values, L, F, and R for left, straight, and right, and the register that associates the hydropathy of each residue with its particular lattice coordinate. Each code of bits in the chromosome 115 of FIG. 5 corresponds to a directional input, which indicates the next direction that the protein folds, and also increments and decrements the x or y lattice coordinate of that residue.

The state machine 705 holds the present state, consisting of the (x, y) coordinate and the direction: North, East, South, or West. The state machine then receives a direction of left, right, or straight ahead, and derives the next state. According to the direction, the (x, y) coordinate is incremented or decremented and the next direction is saved as the next state. Each possible combination of North, East, South, and West, and left, right, and straight ahead is coded in the state machine and produces a next state in response. For example, with a present state of South, a direction of left yields a next state of East and the corresponding (x, y) coordinate is incremented in the x-direction. With a present state of East, a direction of right yields a next state of South and the corresponding (x, y) coordinate is decremented in the y-direction. With a present state of West, a direction of straight ahead yields a next state of West and the (x, y) coordinate is decremented in the x-direction. A corresponding 3-d state machine would also include the directions up and down, as well as a z-axis coordinate.

The logical operation of the 2-d state machine 705 as described hereinabove and illustrated in FIG. 8, generally designated therein by the reference numeral 800, is shown below in Table III.

TABLE III

Logical operation of the 2-d lattice coordinate state machine 800

| Present State | Input | Next State | Action |
| --- | --- | --- | --- |
| N | L | W | x-- |
|   | F | N | y++ |
|   | R | E | x++ |
| S | L | E | x++ |
|   | F | S | y-- |
|   | R | W | x-- |
| E | L | N | y++ |
|   | F | E | x++ |
|   | R | S | y-- |
| W | L | S | y-- |
|   | F | W | x-- |
|   | R | N | y++ |

With reference again to FIG. 7, the information on each residue then enters an n-stage pipeline where each residue's combined coordinate is held in a register associated with the stage and then passed on to the next stage for comparison. For example, the first residue's (x, y, h) coordinate is simply held in a first stage storage register 709. The second residue's (x, y, h) coordinate is held in a temporary register 707 where it is compared with the first residue's (x, y, h) coordinate in comparators 719, 725 then stored in a second stage storage register 713. The third residue's (x, y, h) coordinate is compared with the first residue's (x, y, h) coordinate in the temporary storage register 707 and the second residue's (x, y, h) coordinate in the temporary storage register 711, and then stored in a third stage storage register, and so on. The timing and comparison of each residue with each other residue is explained in more detail in relation with FIG. 9, hereinbelow.

At each stage, a collision comparison 719 and an adjacency comparison 725 are made between the two residue's (x, y, h) coordinates. Collision is detected by lattice coordinate equality for two residues. When a collision occurs, the collision count is incremented 721 and passed to a collision count storage register 723 in the next stage. Adjacency is detected by a difference of 1 in either (but not both) the x or y lattice coordinate and both residues being hydrophobic. As with the collision detection, when an adjacency is detected, the adjacency count is incremented 727 and the resultant value is passed to an adjacency storage counter 729 in the next pipeline stage.

At the end of the pipeline, the collision counts and adjacency counts are totaled in separate accumulators 731 and 733 as positive and negative numbers, respectively. The final folding cost 735 is a composite of the two numbers. If collisions have occurred, the collision number will be the most significant part of the folding cost, since the total collision count is multiplied by a constant that is greater than the total adjacency count. If no collisions have occurred, the negative adjacency count will be sign-extended and it will then represent the folding cost.

Illustrated in more detail using the simple protein of FIG. 5 is the cost determination using the pipelined digital circuit of FIG. 7. As shown in FIG. 5, the protein has 5 residues R1–R5 with a default chromosome of 01101011. Assuming that the protein has an h-template of "b-p-b-b-p", corresponding to R1–R5 in that order, where "b" stands for a hydrophilic residue and "p" stands for a hydrophobic residue, feeding chromosome 01101011 into the lattice coordinate state machine with the h-template will generate the following combined coordinates for each residue in a 2-d lattice:

R1 (0, 0, b); R2 (−1, 0, p); R3 (−1, 1, b); R4 (0, 1, b) and R5 (1, 1, p).

Note that the first residue R1, which is not coded by the chromosome, always has a lattice coordinate of (0, 0). The information on each residue then enters a 5-stage pipeline in this example. The combined coordinate of R1 enters the first stage and is held in the register associated with the first stage 709. The coordinate of R2 then enters the first stage 707 and is compared with R1. Two comparisons are made at this stage. First, the circuit makes a collision comparison 719 between the lattice coordinate of R1 and R2. If the two residues have the same lattice coordinate, it would suggest that R2 is trying to move into the lattice position occupied by R1. This is defined as a collision and the collision counter 721 will register a "1". Otherwise, the collision counter 721 will register a "0". The circuit 700 then makes an adjacency comparison 725 where the hydropathy and coordinates of R1 and R2 are compared 725 in the context of their respective lattice coordinates. By definition, two hydrophobic residues are "adjacent" only when they are next to each other horizontally or vertically, but not diagonally. Therefore, the circuit will simultaneously compare 725 the lattice coordinate and the hydropathy of R1 and R2, the adjacency counter 729 will register a "1" only when the hydropathy in R1 and R2 is each "p", and when R1 and R2 share the same x or y lattice coordinate but not both. For example, two residues with combined coordinates of (0, 1, p) and (1,1, p) would give an adjacency count of 1 but residues with coordinates of (1, 1, p) and (1,1, p) would indicate a collision.

Based on these criteria, the comparison between R1 and R2 will lead to a "0" on both the collision counter 721 and the adjacency counter 727, which are then sent to the collision accumulator 723 and the adjacency accumulator 729, respectively. At the end of the pipeline, the collision counts and adjacency counts are totaled as positive 731 and negative numbers 733 respectively. The two numbers are then added to each other to give a final folding cost 735. After the comparison in the first stage, R2 is stored in the second stage 711.

In the next step, the coordinate of R3 is compared with R1 in the first stage and R2 in the second stage and finally stored in the third stage. The collision and adjacency counts at each stage are forwarded to the collision accumulator and the adjacency accumulator, respectively. The same process is repeated with R4 and R5. At the end of the pipeline, the final folding cost 735 for chromosome 01101011 is 0.

The chromosome will be held as the "default chromosome". The computer will then select another possible chromosome and calculate the folding cost of that chromosome, and compare it to the folding cost of the default chromosome. If the folding cost of the new chromosome is lower than the folding cost of the default chromosome, the new chromosome will become the "default chromosome". If the folding cost of the new chromosome is equal or higher then that of the default chromosome, the computer will keep the default chromosome. The search process will continue until all the possible chromosomes are evaluated and the chromosome or chromosomes with the lowest folding cost is determined. In the present case, a complete evaluation would require 81 crossovers, and chromosomes 01100101, 11011010, 11110101, and 11111010, as well as the corresponding chromosomes 00011010, 00000101, and 00001010, all give the lowest folding cost of −1. In general, a single protein is much larger than 5 residues and is described by many more conformations than 81. In a 2-d 36-residue protein, as described before, the solution space is $5 \times 10^{16}$, and evaluation of every single permutation possible may be impractical or impossible.

Figure 9:
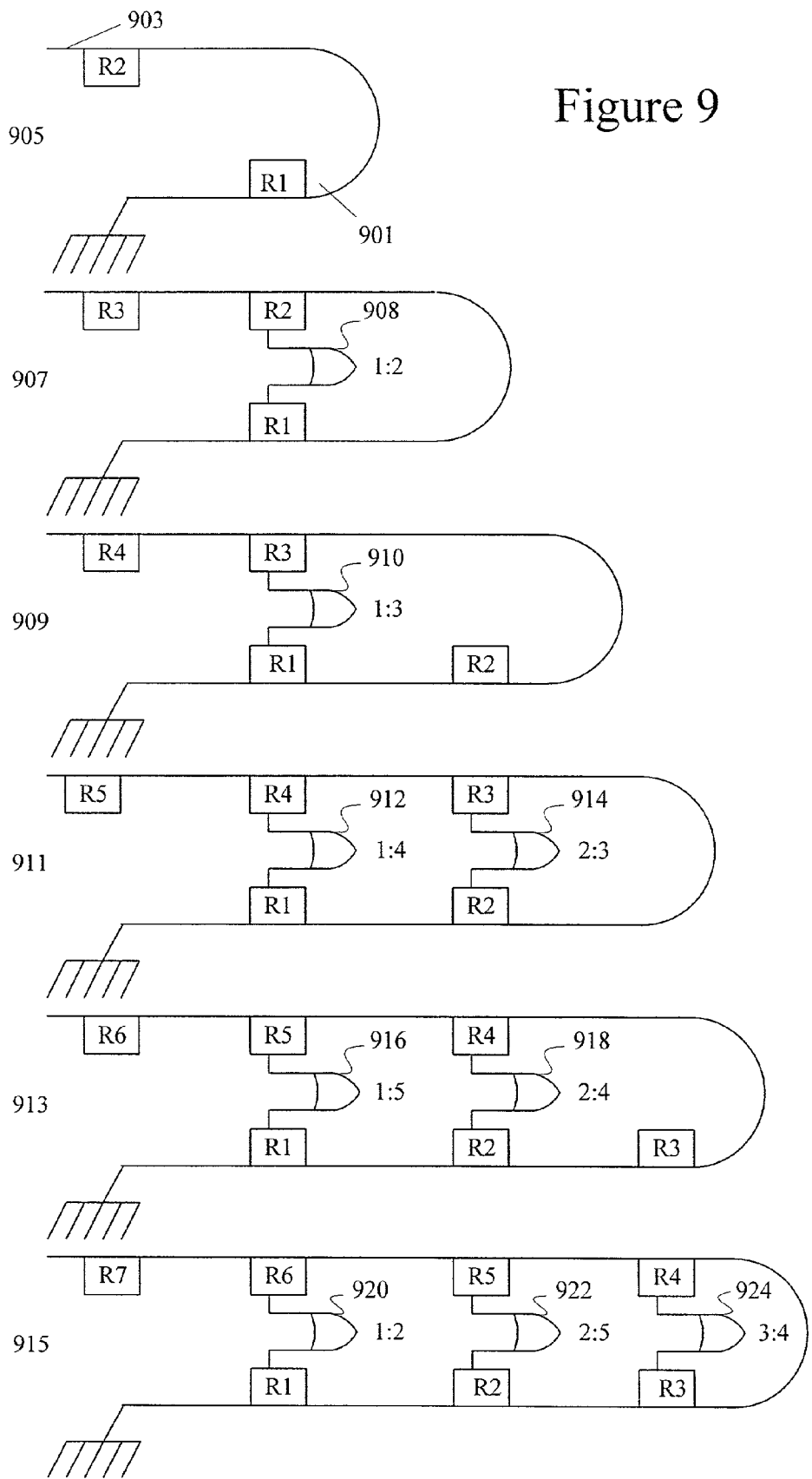
FIG. 9 pictorially explains the operation of the pipeline digital circuit of the present invention.

As shown in FIG. 9, the order of comparison can be more abstractly illustrated. Each residue 901 on a protein string 903 is compared with all other residues. Initially, the residues on the protein string 903 are not related (step 905). As the string folds, residues R1 and R2 are then compared (step 907) by a comparator 908. As the string folds further, residues R1 and R3 are compared (step 909) by another comparator 910. The protein string 903 folds further and further (steps 911, 913, and 915), until eventually all the residues are compared to their corresponding residues by respective comparators 912, 914, 916, 918, 920, 922 and 924.

Figure 10:
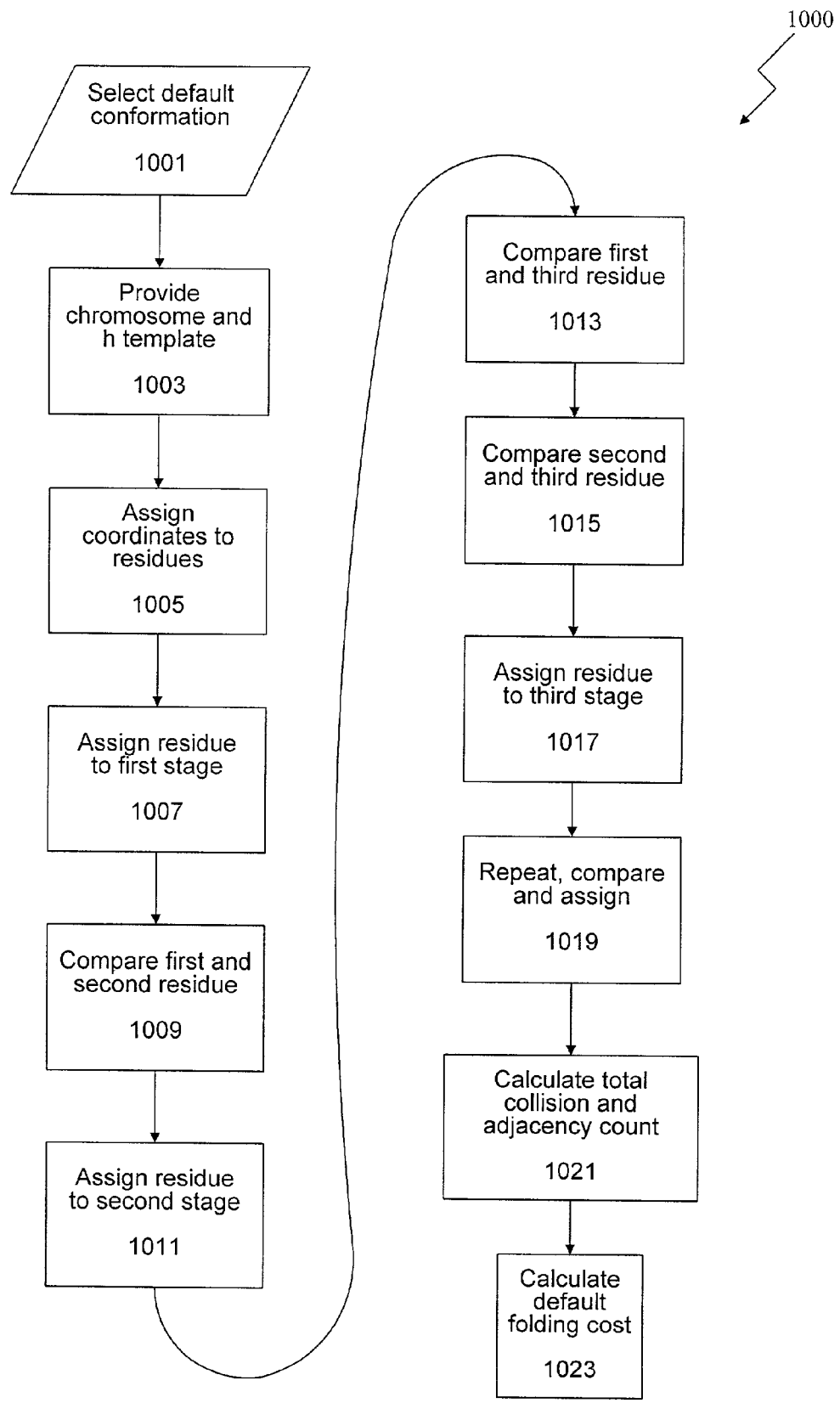
FIG. 10 illustrates a flowchart showing a representative operation performed by the pipeline digital circuit of the present invention.

With reference now to FIG. 10, there is illustrated a process of calculating folding cost, generally designated by the reference numeral 1000. The process 1000 includes the following steps: providing a default conformation for a protein with n residues (1001); providing a chromosome and a hydropathy template, each corresponding to the protein with the default conformation (1003); assigning a coordinate to each residue based on said chromosome and hydropathy template (1005); assigning the coordinate of a first residue to a first stage (1007); comparing the coordinate of a second residue to the coordinate of the first residue to determine a collision count and an adjacent count (1009); assigning the coordinate of the second residue to a second stage (1011); comparing the coordinate of a third residue to the coordinate of the first residue to determine a collision count and a adjacent count in the first stage (1013), and to the coordinate of the second residue to determine a collision count and an adjacent count in the second stage (1015); assigning the coordinate of the third residue to a third stage (1017); repeating this comparison process until the coordinate of the last residue n is stored in stage n (1019); calculating a total collision count and a total adjacent count (1021); and calculating a default folding cost based on the total collision count and the total adjacent count (1023).

Figure 11:
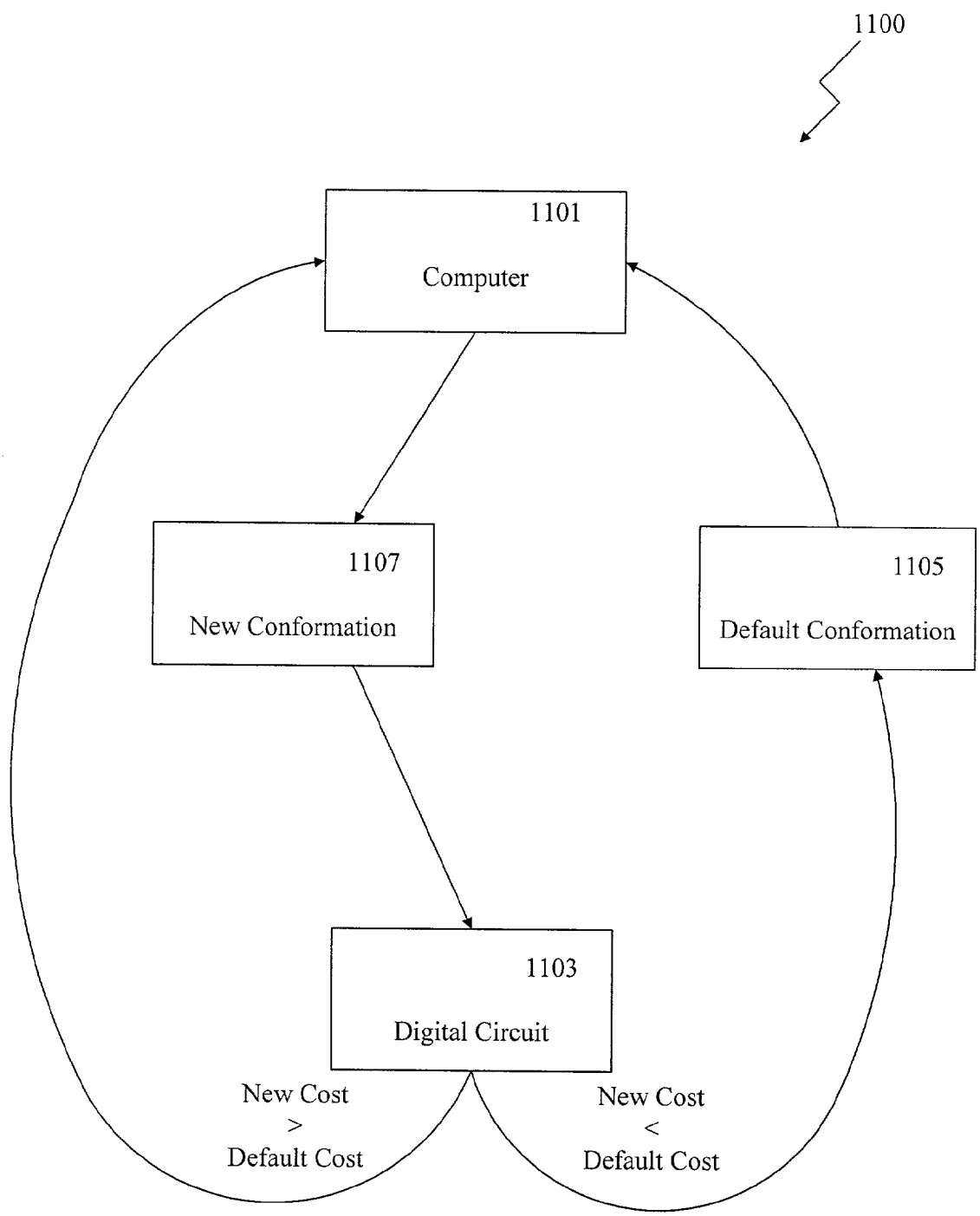
FIG. 11 illustrates a flowchart of a representative search process for the conformation with the lowest folding cost.

With reference now to FIG. 11, there is illustrated a search process for the conformation with the lowest folding cost, generally designated by the reference numeral 1100. For a given protein in a 2-d lattice model, a computer 1101 will arbitrarily select a default conformation, generally designated by the reference numeral 1105, and calculate through the pipelined digital circuit 1103 a folding cost for the default conformation (default cost). The computer 1101 then selects another possible conformation 1107, either randomly or through a genetic algorithm, and calculates the folding cost of the new conformation (new cost). If the new cost is lower than the default cost, the new conformation 1107 becomes the default conformation 1105. If the new cost is higher than the default cost, the computer 1101 will select a different conformation and start over again. Theoretically, this process may be repeated until all the possible conformations of the given protein have been evaluated and the default conformation is the conformation with the lowest folding cost. In actuality, with an extremely large number of possible conformations, every possible conformation is not evaluated; rather, the computer 1101 evaluates a pre-determined number of conformations and arrives at a lowest folding cost of the conformations evaluated.

The pipelined cost function circuit may receive randomly generated chromosomes or may receive chromosomes from a genetic algorithm computer that generates child chromosomes through combinations of parent chromosomes. In the genetic algorithm computer, more-fit child chromosomes replace the less-fit parent chromosomes, the general population increases, and the population tends to converge wholly upon a best solution. In the latter case, parameters of the genetic algorithm may be altered prior to and during each simulation. These parameters include the possibility that any one bit will be the site of a crossover, i.e., the point at which one parent chromosome breaks off and the other parent chromosome continues in generating the child chromosome, and the possibility that any one bit will be the site of mutation, i.e., any bit in the child chromosome may be mutated or flipped, 1 to 0 or 0 to 1, to add diversity to the population of chromosomes.

Figure 12:
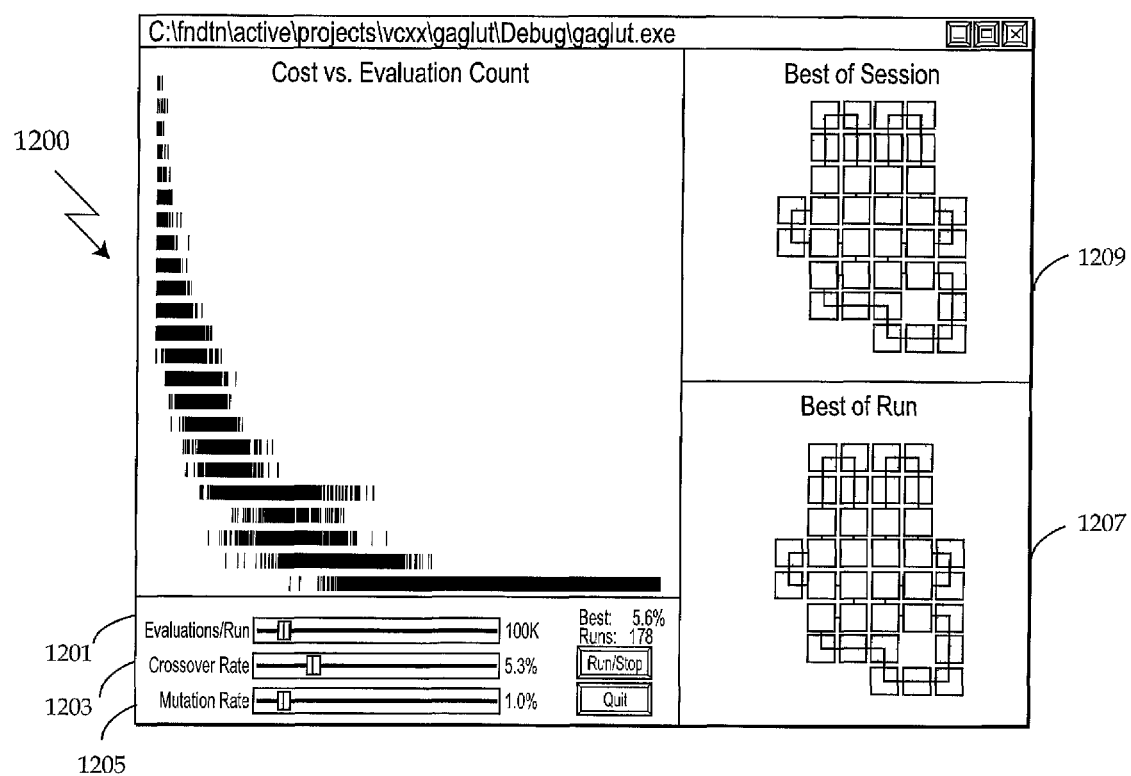
FIG. 12 shows a real-time control screen of a genetic algorithm using the pipeline digital circuit of the present invention.

With reference now to FIG. 12, there is illustrated a representative experiment control screen 1200. The experiment is designed to run in real time with the experimenter varying the evaluations per run, crossover probability, and mutation probability via respective sliders 1201, 1203 and 1205 on the control screen 1200 as the problem is repeatedly run with new random population initializations. In this case, the length of the simulation is determined by the evaluations per run value. Running at 66 MHz with a run-length limit of 100,000 crossovers, for example, provides a display update rate of 36.67 Hz (i.e., 36.67 100,000-crossover runs/sec). At this rate the experimenter can effectively "tune in" the optimal crossover and mutation parameters in real time by watching the shape of the cost curve change as a function of parameter settings.

FIG. 12 shows a run of the problem with a population of 512, cutpoint probability 1203 of 5%, and a mutation probability 1205 of 1%. A pattern of hydrophobic residues in the 36-residue protein used in the experiment is shown in the Best of Run display 1207, and the optimal conformation of this protein as defined by the minimal energy grouping of hydrophobic residues is shown in the Best of Session display 1209. Because the Best of Run display 1207 and the Best of Session display 1209 are identical, the particular probability settings are tuned in to the optimal solution.

By virtue of the improvements set forth in the present invention, the lattice-based protein folding problem has been accelerated by approximately 10,000 times. Even at moderate accelerations demonstrated by the modest prototype incorporating only one cost function, a speedup of 320 times is possible for a 36-residue protein. This permits real-time tuning of problem parameters by the experimenter.

As discussed above, the pipelined cost function has an initiation interval of n or 36 clock cycles in the case of this example. With a single cost circuit, an exemplary implementation achieved an acceleration of 320 times over a 366 MHz Pentium II running the same algorithm in C. However, when the pipeline initiation interval is greater than 1, multiple units can be implemented up to the limit imposed by the initiation interval or chip area limitations. By implementing a design with 30 cost function units in a Xilinx XCV3200E FPGA, an acceleration of 9,600 times could be obtained.

Although preferred embodiments and their advantages have been described in detail, various changes, substitutions and alterations can be made herein without departing from the scope of the sintering process as defined by the appended claims and their equivalents.

What is claimed is:

1. A computer-assisted methodology for determining the conformational energy of a folded protein comprising the steps of:
    (a) inputting a potential conformation for a protein with a plurality of residues into a state machine;
    (b) receiving from the state machine spatial coordinates of each residue corresponding to the potential conformation for the protein;
    (c) comparing the spatial coordinates and corresponding hydropathy of each residue to each other residue at least once using pipelined comparators to determine a collision count and an adjacency count;
    (d) calculating a total collision count and total adjacency count from the pipeline of comparators;
    (e) calculating a folding cost based on the total collision count and the total adjacent count; and
    (f) replacing a default conformation with the potential conformation if the potential folding cost associated with the potential conformation is lower than a default folding cost.

2. The methodology according to claim 1, further comprising the step of:
    (g) repeating steps (b) to (f) a plurality of times.

3. The methodology according to claim 1, wherein said folding cost is the sum of said total collision count and said total adjacency count.

4. The methodology according to claim 3, wherein said total collision count is positive.

5. The methodology according to claim 3, wherein said hydropathy for each residue is hydrophobic or hydrophilic.

6. The methodology according to claim 5, wherein said total adjacency count is negative for hydrophobic residues.

7. An apparatus for determining the conformational energy of a folded protein having a plurality of residues and a default conformation comprising:
    means to assign a spatial coordinate to each residue of said protein in a potential conformation;
    means for using a pipeline to determine a collision count and an adjacent count for each residue;
    means to determine a total collision count and a total adjacent count for the potential conformation having said plurality of residues;
    means to determine a folding cost for the potential conformation; and
    means to compare the folding cost of the default conformation with the folding cost of the potential conformation.

8. The apparatus according to claim 7, further comprising:
    means for replacing the default conformation with the potential conformation.

9. The apparatus of claim 8, wherein said means for replacing the default conformational energy of the folded protein occurs a plurality of times.

10. The apparatus according to claim 7, wherein said total collision count is positive.

11. The apparatus according to claim 7, wherein said total adjacency count is negative.

12. A fitness circuit for determining the fitness of a conformation for a protein folding problem, said fitness circuit comprising:
    a conformation register containing a potential conformation for said protein folding problem therein;
    a hydropathy register containing an associated hydropathy for each residue of said potential conformation;
    a state machine, said state machine determining spatial coordinates and associated hydropathy for said residues of said potential conformation;
    a plurality of pipelined comparators comparing the spatial coordinates and associated hydropathy of a respective residue with another residue of said potential conformation, said plurality of pipelined comparators determining a collision count and an adjacency count of said respective residue with said another residue; and an adder connected to each of said plurality of pipelined comparators, said adder adding said collision count and said adjacency count, thereby determining the fitness of said potential conformation for said protein folding problem.

13. The fitness circuit according to claim 12, wherein said collision count is positive.

14. The fitness circuit according to claim 12, wherein said hydropathy for each residue is hydrophobic or hydrophilic.

15. The fitness circuit according to claim 12, wherein said adjacency count is negative for hydrophobic residues.

16. A method for determining the fitness of a conformation for a folded protein problem, said method comprising the steps of:

inputting a potential conformation for a folded protein with a plurality of residues into a state machine;

receiving from the state machine spatial coordinates of each residue corresponding to the conformation for the folded protein;

comparing using a pipeline the spatial coordinates and corresponding hydropathy of each residue to each other residue at least once to determine a collision count and an adjacency count;

calculating a total collision count and total adjacency count result from the pipeline; and calculating a folding cost based on the total collision count and the total adjacency count.

17. The method according to claim 16, wherein said folding cost is the sum of said total collision count and said total adjacency count.

18. The method according to claim 16, wherein said total collision count is positive.

19. The method according to claim 16, wherein said hydropathy for each residue is hydrophobic or hydrophilic.

20. The method according to claim 19, wherein said total adjacency count is negative for hydrophobic residues.

* * * * *